(12) United States Patent
Guetlhuber et al.

(10) Patent No.: US 7,521,029 B2
(45) Date of Patent: Apr. 21, 2009

(54) SHELL-AND-TUBE TYPE REACTOR FOR CARRYING OUT CATALYTIC GASEOUS PHASE REACTIONS AND A PROCEDURE FOR OPERATING THE SAME

(75) Inventors: Friedrich Guetlhuber, Neubiberg (DE); Manfred Lehr, Deggendorf (DE)

(73) Assignee: MAN DWE GmbH, Deggendorf (DE)

( * ) Notice: Subject to any disclaimer, the term of this patent is extended or adjusted under 35 U.S.C. 154(b) by 874 days.

(21) Appl. No.: 10/541,698

(22) PCT Filed: Jan. 31, 2003

(86) PCT No.: PCT/EP03/00977

§ 371 (c)(1),
(2), (4) Date: Jul. 7, 2005

(87) PCT Pub. No.: WO2004/067164

PCT Pub. Date: Aug. 12, 2004

(65) Prior Publication Data
US 2006/0133972 A1  Jun. 22, 2006

(51) Int. Cl.
F28D 7/00 (2006.01)
B01J 19/00 (2006.01)
B01J 10/00 (2006.01)
B01J 8/04 (2006.01)
G05D 16/00 (2006.01)

(52) U.S. Cl. ........................ 422/201; 422/198; 422/196; 422/103; 422/113; 422/186.14; 137/15.06; 137/68.14; 261/114.4; 261/38; 261/42; 261/44.3

(58) Field of Classification Search ................. 422/201, 422/198, 196, 103, 113, 186.14; 137/15.06, 137/68.14; 261/114.4, 38, 42, 44.3
See application file for complete search history.

(56) References Cited

U.S. PATENT DOCUMENTS 5,286,455 A * 2/1994 Eilers et al. .................. 422/110

(Continued)

FOREIGN PATENT DOCUMENTS

DE       1667247 (A1)      *   9/1971

(Continued)

OTHER PUBLICATIONS

Handbuch des Explosionsschutzes, herausgegeben von Henrikus Steen.

*Primary Examiner*—Walter D Griffin
*Assistant Examiner*—Natasha Young
(74) *Attorney, Agent, or Firm*—Milde & Hoffberg, LLP

(57) ABSTRACT

The invention relates to a tubular reactor for carrying out catalytic gas-phase reactions, containing a catalyst tube bundle (8) that is traversed by the relevant reaction gas mixture, is filled with a catalyst, extends between two tube sheets (4, 148) and around which flows a heat transfer medium contained within a surrounding reactor jacket (6). The reactor also comprises gas entry and discharge hoods (2; 60) that cover the two tube sheets for supplying the relevant process gas to the catalyst tubes and for discharging the reacted process gas from the catalyst tubes. Together with all the parts that come into contact with the process gas mixture, the reactor is designed to have an appropriate strength for withstanding the deflagration and explosive pressures that are to be taken into account during its operation. The volume available to the process gas mixture prior to its entry into the catalyst tubes is restricted as much as possible in construction and flow engineering terms.

45 Claims, 9 Drawing Sheets

U.S. PATENT DOCUMENTS

2003/0017095 A1    1/2003    Olbert et al.

FOREIGN PATENT DOCUMENTS

| DE | 198 06 810 | A1 | | 2/1998 |
|---|---|---|---|---|
| DE | 198 07 018 | A1 | | 2/1998 |
| DE | 100 21 986 | A1 | | 5/2000 |
| DE | 20301515 (U1) | | * | 7/2003 |
| EP | 1 180 508 | A1 | | 8/2001 |
| WO | WO 03/022418 | A1 | | 3/2003 |

* cited by examiner

SHELL-AND-TUBE TYPE REACTOR FOR CARRYING OUT CATALYTIC GASEOUS PHASE REACTIONS AND A PROCEDURE FOR OPERATING THE SAME

BACKGROUND OF THE INVENTION

The invention relates to a shell-and-tube type reactor for carrying out catalytic gaseous phase reactions that comprises: (a) a bundle of contact tubes through which the relevant reaction gas mixture flows, that extend between a gas intake-side tube sheet and a gas output-side tube sheet, that contain a catalytic filling, and that are flushed by a heat transfer medium inside a surrounding reactor shell; (b), a gas intake hood and a gas outlet hood spanning the two tube sheets, respectively, for providing the relevant process gas to the contact tubes and for evacuating the reacted process gas from the contact tubes; and (c) a process gas main pipe for feeding the process gas into the gas intake hood.

Such a shell-and-tube type reactor is generally known from the German Patent No. DE 100 21 986.1. In that specific case however the endeavor to reduce the risk of deflagration has led the inventor, to some extent, to feed a critically explosive component of the process gas brought to reaction in the reactor only immediately before or even in the reaction tubes. Moreover, the volume available to that component is until then kept to a minimum, for instance with a fitting inserted into an otherwise conventional more or less spherical cap-shaped gas intake hood. These measures are based on the following insights:

1) In order to attain the greatest possible production capacity in relation to the size of the reactor system it is desirable to be able to maximize the process gas charge with the critically explosive components such as oxygen and hydrogen.

2) The risk of a deflagration increases, besides in relation to the charge, with the amount of time in which the two components are both resident in the same space.

There have previously been attempts to guard against extensive damages from any eventually occurring deflagrations by installing rupture disks in reactor systems. But if the aim is to further increase the charge and thus the output as well then the use of rupture disks is inadequate in view of the heightened risks of deflagration. Replacement of the rupture disks, expensive enough in themselves, in the case of a deflagration requires relatively protracted repair work and concomitantly protracted down times. The rupture of rupture disks is connected with a blast wave which can be heard miles away as a bang and simply for that reason is unacceptable. In addition noxious gases can escape into the environment. Moreover, after a deflagration and the concomitantly necessitated replacement of the rupture disks the re-starting of the reactor required in each case is difficult and time-consuming, especially since during the build-up to a greater charge in operating mode care must be taken that passing through the deflagration range of the gas mixture currently being fed into the reactor is avoided.

Such a deflagration range can be illustrated in a two or three-component diagram like the one shown in *Handbuch des Explosionsschutzes* by Henrikus Steen (Verlag Wiley-VCH, 1st Ed, 2000, page 332) where the third component is an inert gas added for dilution such as nitrogen. It has been shown that the danger of a deflagration only obtains within a window-like range that is moreover dependent upon pressure, temperature and geometry.

According to DE 198 06 810 A1 the temperature of the tube sheet on the gas intake side can be reduced by a heat insulation layer applied to it in order to prevent hazardous lateral reactions including ignition and deflagration.

EP 1 180 508 A1 shows how to avoid the deflagration range through constant measurement and modification of the process gas composition during startup of a reactor, in which case initially an inert gas is added that is then successively replaced by already reacted process gas after the reaction sets in.

SUMMARY OF THE INVENTION

The present invention is based in the first instance on the problem of being able to increase the charge of process gas to be moved forward to reaction in a risk-less and additionally economic manner.

This problem is solved, according to the invention by providing a shell-and-tube type reactor wherein the process gas main pipe comprises a first section, in which the process gas is in a non-explosive range, and in process gas flow direction behind it a second section, in which the process gas is in an explosive range; wherein the process gas main pipe comprises in its first section a check valve arrangement; and wherein the check valve arrangement and the gas intake-side tube sheet, and all parts therebetween, which bear the process gas pressure under normal operation conditions, are designed to withstand the maximum pressure caused by a deflagration or detonation.

Secondly the invention is based on the problem of operating a shell-and-tube type reactor according to the invention by taking commercial advantage of its special properties. This problem is solved by a process wherein at least one of the feed-in points is arranged to receive the associated process gas component in a liquid form and/or wherein said at least one feed-in point has means for injecting the liquid process gas component.

The reactor of the invention may for one thing even be operated with a critically explosive charge of the process gas to be moved forward to reaction, for another thing by going through an ignitable range during startup, something that significantly facilitates and accelerates the process of startup.

For the following considerations a distinction must be made between a deflagration and a detonation (or explosion), a distinction that nonetheless was not made in the previously cited EP 1 180 508 A1 which was based on a translation from Japanese. In contrast to deflagration that is set off at one point and provokes a blast wave traveling at subsonic speed, a detonation is a considerably more sudden and consequently violent process that in most cases presupposes, besides an even more special gas mixture, a deflagration preceding it that can develop over a specific design-related starting or entry region.

For a full understanding of the present invention, reference should now be made to the following detailed description of the preferred embodiments of the invention as illustrated in the accompanying drawings.

DESCRIPTION OF THE PREFERRED EMBOBIMENTS

Figure 1:
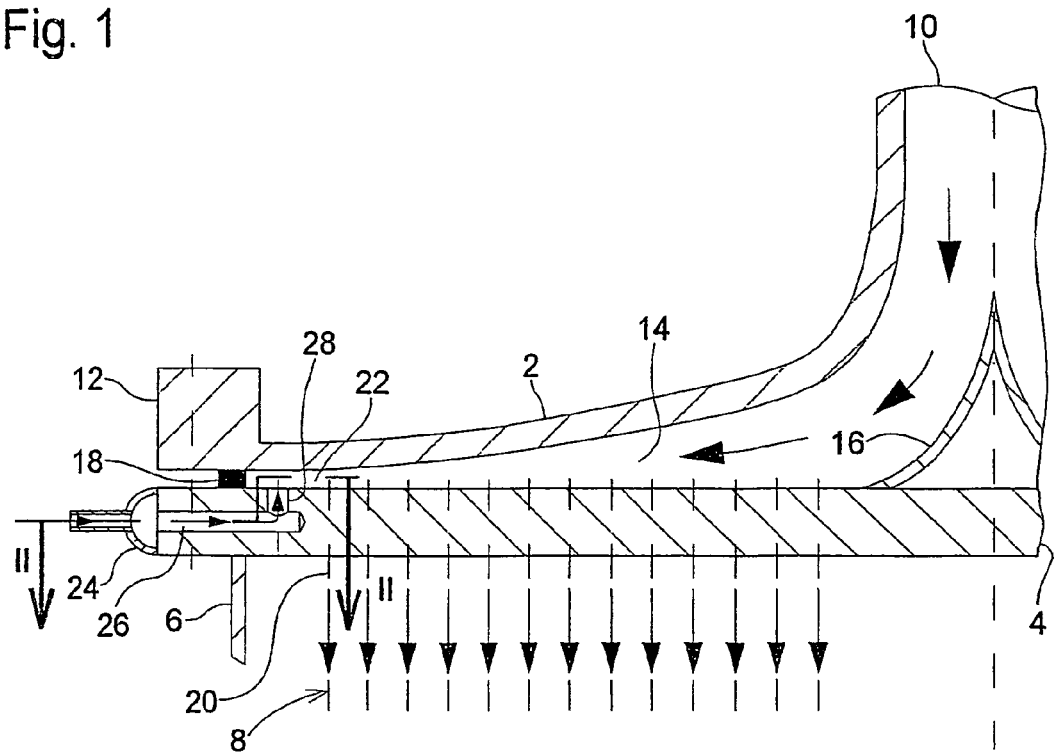
FIG. 1 shows a tube sheet on the gas intake side together with a gas intake hood of a shell-and-tube type reactor according to the invention in a longitudinal half-section.

The preferred embodiments of the present invention will now be described with reference to FIGS. 1-11 of the drawings. Identical elements in the various figures are designated with the same reference numerals.

FIG. 1 shows somewhat schematically the gas intake end of a shell-and-tube type reactor according to the invention for carrying out catalytic gaseous phase reactions in the critical range for deflagrations or even detonations. More precisely stated, in FIG. 1 a specially designed gas intake hood 2, a tube sheet 4 underneath it, the reactor shell 6 adjacent to it, a ring-shaped contact tube bundle 8 (hinted at here by a broken line) and gas intake pipe socket or nozzle 10 leading into the gas intake hood 2 can all be recognized. In the usual manner, the tube bundle 8 containing a suitable catalyst filling is irrigated within the reactor shell 6 by a heat transfer medium which is—in any case in operation—liquid and via which throughout the contact tubes a suitable temperature profile is maintained and excess reaction heat is led off.

As can be further seen from FIG. 1, the gas intake hood 2, apart from a massive peripheral collar serving its attachment to and sealing-off of the tube sheet 4, is relatively flat and somewhat trumpet funnel-shaped so that between it and the tube sheet 4 there is a, flat gas distribution space 14 connected evenly, that is without steps, kinks or so forth, to the gas intake pipe socket or nozzle 10. Attachment of the gas intake hood 2 to the tube sheet 4 is accomplished via studs positioned around it which are only hinted at here.

The gas distribution space 14 is dimensioned in such a way that the process gas fed into the contact tubes through it flows as evenly as possible into the contact tubes, i.e. in order to minimize turbulence as well as residence time. In doing so, the design of the gas distribution space may approximately be such that the radial flow component or even the static pressure in the process gas remains constant in the radial direction. Mixed forms are also feasible, and on the other hand the trumpet funnel shape of the gas intake hood 2 can be approximated as well by more or less conical ring elements (not shown). To produce evenness in the gas flow at the entry to the gas distribution space 14, a spike-shaped flow diverter 16 is arranged there underneath the gas intake pipe socket or nozzle 10 and resting on the tube sheet 4, which simultaneously constitutes a displacer in order to prevent the gas from impacting frontally in the middle of the tube sheet 4. The minimum height of the gas distribution space 14 is determined in the example shown by a sealing ring 18 of defined dimensions with which the gas distribution space 14 is sealed off from the outside. It is determined in the planning stage and must in any case be big enough so that at no point in the reactor circumference does it become zero, for example because of unevenness in the hood 2 and/or the tube sheet 4. Where required, the hood and/or the tube sheet must be smoothed or faced at the same point.

Since however a dead space 22 can hardly be avoided by design outside of the radially outermost contact tubes, as for example 20, but inside the gas distribution space 14 without obstructing the entry of gas into the radially outermost contact tubes and since such a dead space would entail undesirable residence of the process gas, measures have been taken at these points to displace the process gas out of the dead space 22 or at least to "dilute" it to a composition not critical for deflagration. This is done by injecting gas which is deactivating in regard to the deflagration reaction feared. This could be an inert gas such as N2, a by-product produced in the course of the operative reaction such as CO2, occasionally simply air or even a mixture of such gases.

According to FIG. 1 the gas in question, referred to here below as flushing gas, is injected via a circular pipe 24 on the periphery of the tube sheet 4, from thence inwards to junction canals 26 branching off at regular intervals along the periphery of the tube sheet 4 and then via nozzle bores 28 branching off upwards from the junction canals 26.

Figure 2:
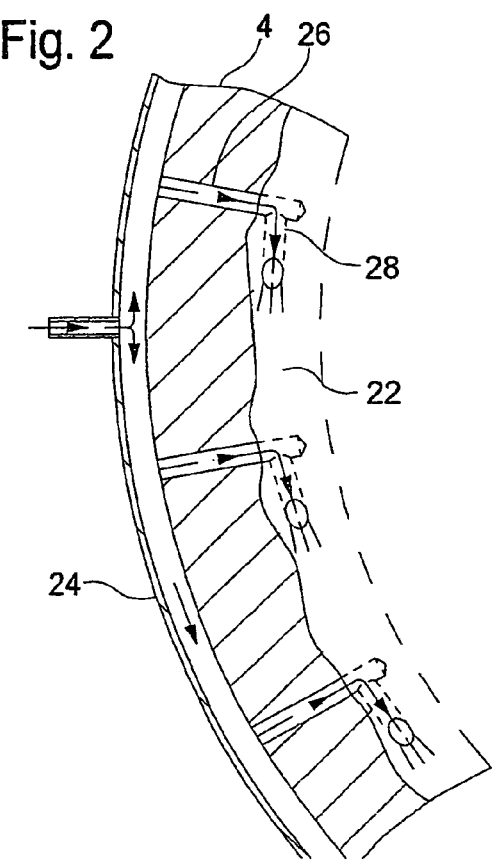
FIG. 2 shows a cross-section through the edge of the tube sheet shown in FIG. 1 at the level of Line II-II in FIG. 1.

As can be recognized from FIG. 2, the nozzle bores 28 slope in the peripheral direction of the tube sheet 4 in order to give the gas exiting from it a radial flow component and, in that way, to flush it through the dead space 22.

Figure 3:
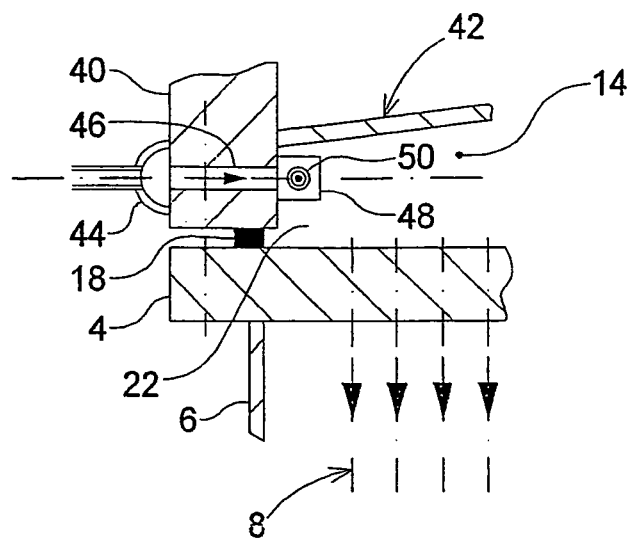
FIG. 3 and FIG. 4 show details similar to those in FIG. 1 and FIG. 2 but with an embodiment with a fitting inserted into a conventional gas intake hood for feeding in process gas.
Figure 4:
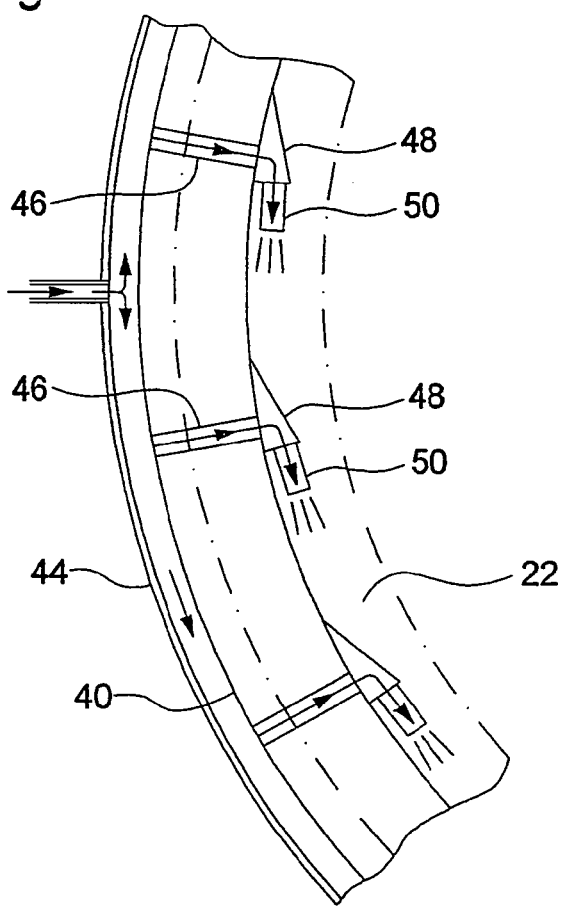

FIG. 3 and FIG. 4 show another embodiment of the gas intake end of a shell-and-tube type reactor according to the invention. Here inside a conventional shell-shaped gas intake hood, of which only the edge 40 is shown here, a fitting restricting the gas distribution space 14 can be recognized. (Where the parts shown here and below are identical to those in FIG. 1 and FIG. 2 they have the same reference numbers).

In a further departure from the embodiments described earlier, here a circular pipe 44 for flushing gas to be led into the dead space 22 surrounds the edge 40 of the gas intake hood and accordingly junction canals similar to the junction canals 26 extend radially through the edge 40. The junction canals 46 run into nozzle caps 48 arranged on the inside of the edge 40 with tangentially aligned nozzles 50 for gas output, likewise to flush out the dead space 22 as much as possible.

Figure 5:
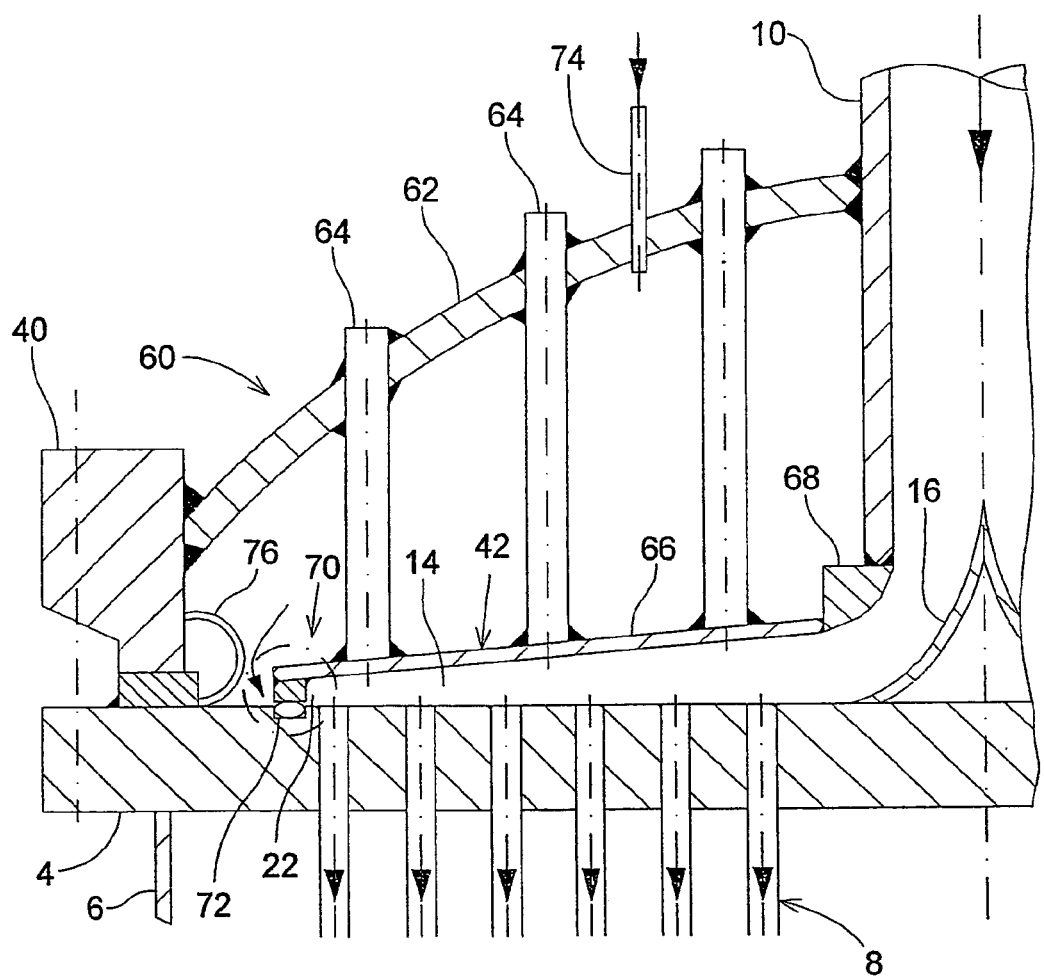
FIG. 5 shows a semi-longitudinal section similar to the one in FIG. 1 through the tube sheet on the gas intake side and a conventional shell-shaped gas intake hood and a fitting inserted into it similar to the one in FIG. 3.
Figure 6:
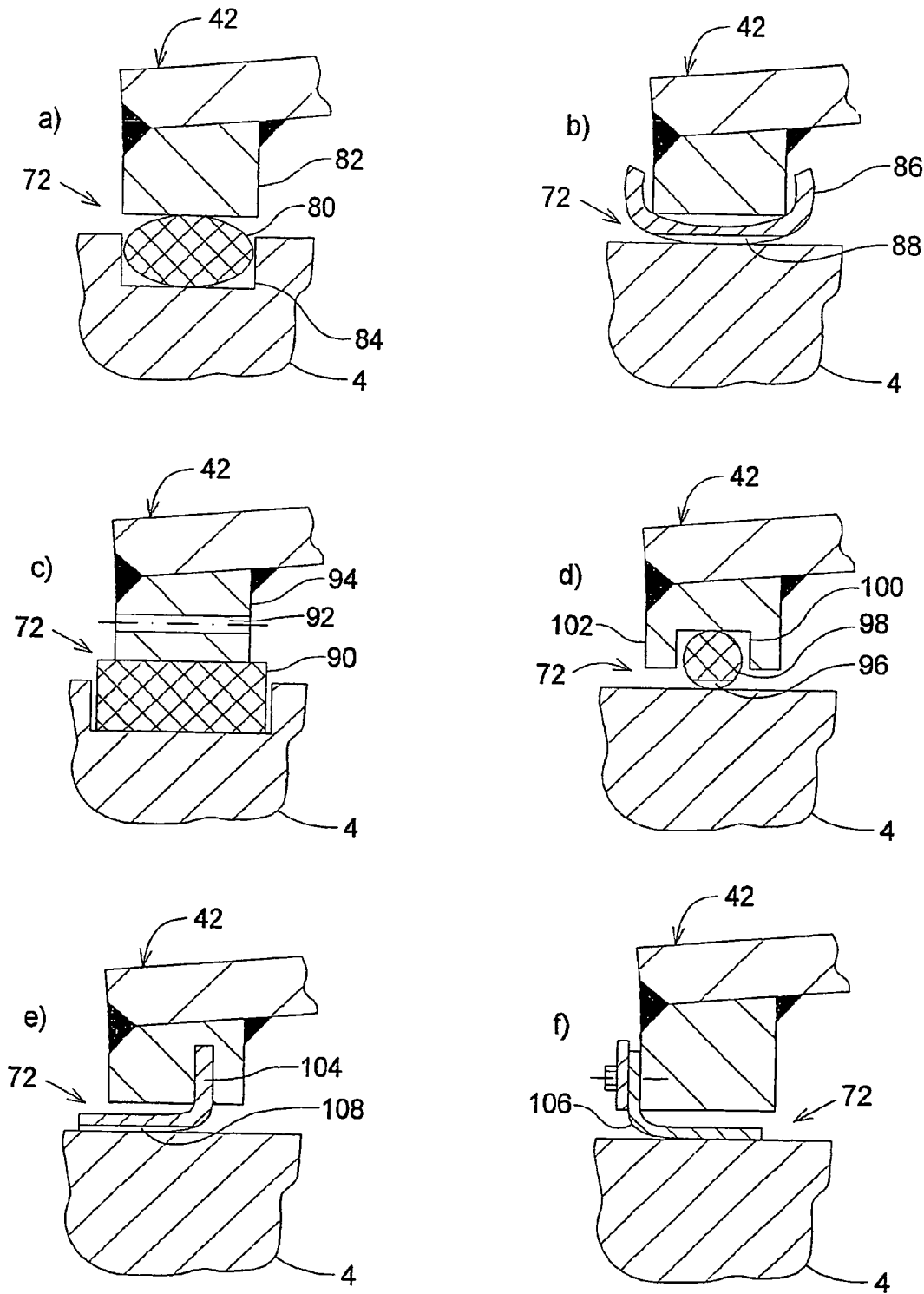
FIG. 6a) through FIG. 6f) show in each case an embodiment of a partially permeable seal as illustrated in FIG. 5, in a larger scale.

FIG. 5 shows an arrangement similar to that of FIG. 3 to the extent that here too a fitting 42 is provided for inside the shell-shaped gas intake hood. As can be seen, the fitting 42 is freely suspended on the gas intake hood 60, more precisely on its shell 62, anchored by means of stud bolts 64 as well as by the gas intake pipe socket or nozzle 10 in such a way that deflagration or detonation forces possibly occurring in the gas distribution space 14 are led into the shell 62. In order to absorb these forces as well as possible, the shell 62 is shaped like a spherical cap.

In this exemplary embodiment the fitting 42 is composed of a slightly conical ring disk 66 and a profile ring 68 rounded off inwards and downwards and is supported at its edge 70 via a partially permeable seal 72 on the tube sheet while the gas intake hood 60 is filled up outside of the fitting 42 with the flushing gas for the dead space 22. From thence the flushing gas enters evenly, to the same extent as it is fed on an ongoing basis to the gas intake hood via a pipe 74, into the dead space 22 via the partially permeable seal 72 around it.

The gas intake hood 60, more precisely its massive edge 40, is sealed against the tube sheet 4 in this example via a type of welded lip seal 76 similar to that described in DE 44 07 728 C1. Actually here too a sealing ring such as the sealing ring 18 from the previously described embodiments could be used. Preferably the flushing gas stands in a relation to the external atmosphere as well, naturally enough, as in relation to the gas distribution space 14 under high pressure in order to function as a blocking medium.

FIG. 6*a*) through FIG. 6*f*) show variously different currently considered embodiments for the partially permeable seal 72 from FIG. 5. According to FIG. 6*a*) the partially permeable seal 72 consists of a ring 80, of itself of a circular or even already elliptical cross-section made from a porous and slightly compressible material such as, for instance, graphite tissue compressed from a ring-shaped projection 82 of the fitting 42 into a corresponding ring groove 84 of the tube sheet 4. According to FIG. 6*b*) the seal 72 consists of a C-shaped profiled and preferably metallic hoop 86 having on its outside towards the tube sheet 4 a number of regularly spaced radial or even somewhat tangential furrows 88; and according to FIG. 6*c*) the seal consists of a massive elastic sealing ring 90 similar to sealing ring 18 in connection with radial or even somewhat tangential bore holes 92 in a projection 94 similar to the projection 82 in FIG. 6*a*). According to FIG. 6*d*) the seal 72 is formed from a ring 98 provided with radial or somewhat tangential furrows 96 and having a basically round cross-section and being formed of metal or of another hard elastic material, the ring lying in a ring groove 100 inside a projection 102 similar to the projection 82. According to FIGS. 6*e*) and 6*f*) sheet profile rings 104 or 106 or angled cross-sections are used as seals 72 which in turn and as emerges from FIG. 6*e*) can have furrows 108 to the tube sheet 4 similar to the furrows 88. Such profile rings can be flexible in regard to high pressure impacting on one side in order to open up for the flushing gas a smaller or greater flow-through cross-section.

Figure 7:
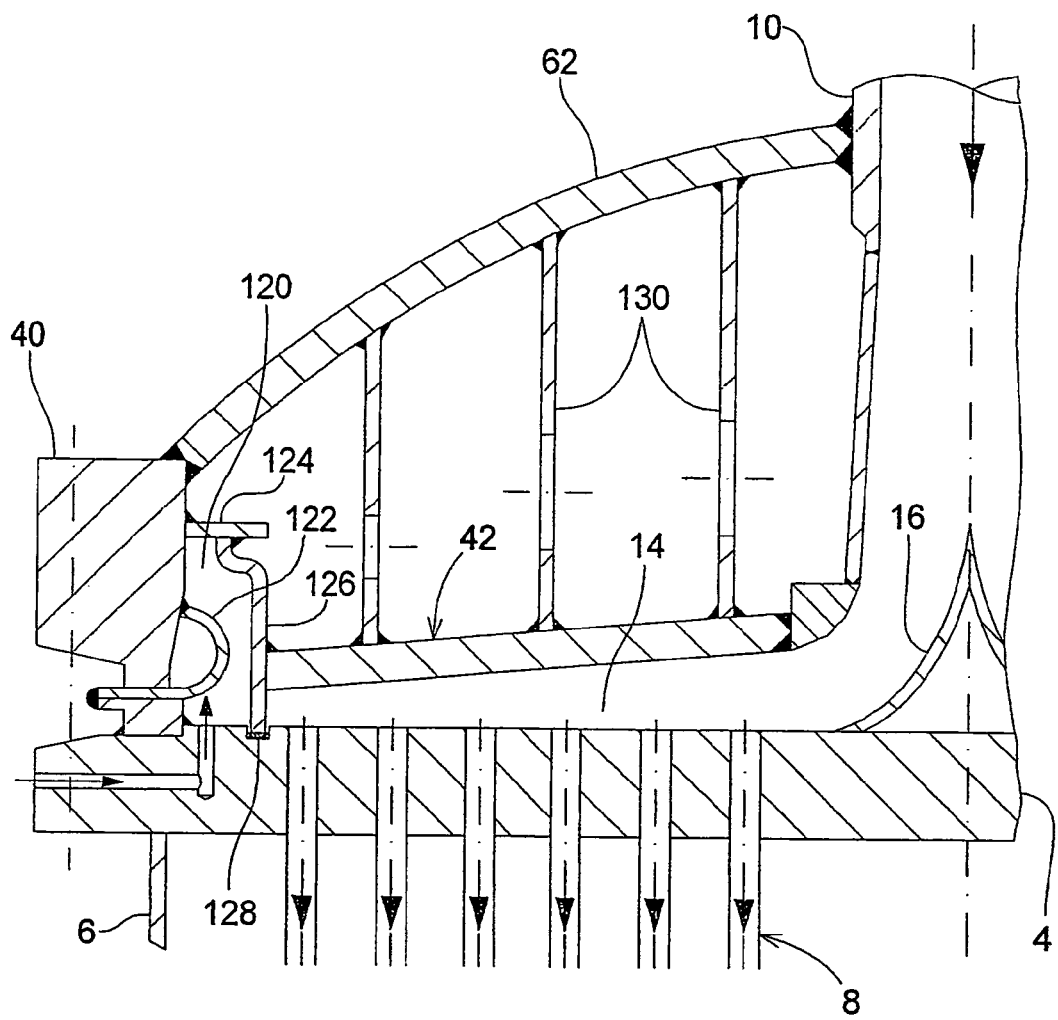
FIG. 7 shows a similar illustration as FIG. 5 but with another embodiment.

FIG. 7 shows an arrangement similar to the one shown in FIG. 5 where however the flushing gas enters radially through the tube sheet 4 into a ring-shaped space 120 between a welded lip seal 122 similar to the welded lip seal 76 and two closely connected sheet rings 124 and 125 outside of the fitting 42. The essentially cylindrical sheet ring 126 attached tightly to the edge of the fitting 42 extends when loose into a ring groove 128 of the tube sheet 4 in order to, in that manner, form a partially permeable seal in relation to the gas distribution space 14, similar to the partially permeable ring 72 known from FIG. 5. The stud bolts 64 known from FIG. 5 are replaced in this example by pierced cylindrical sheets 130.

Figure 8:
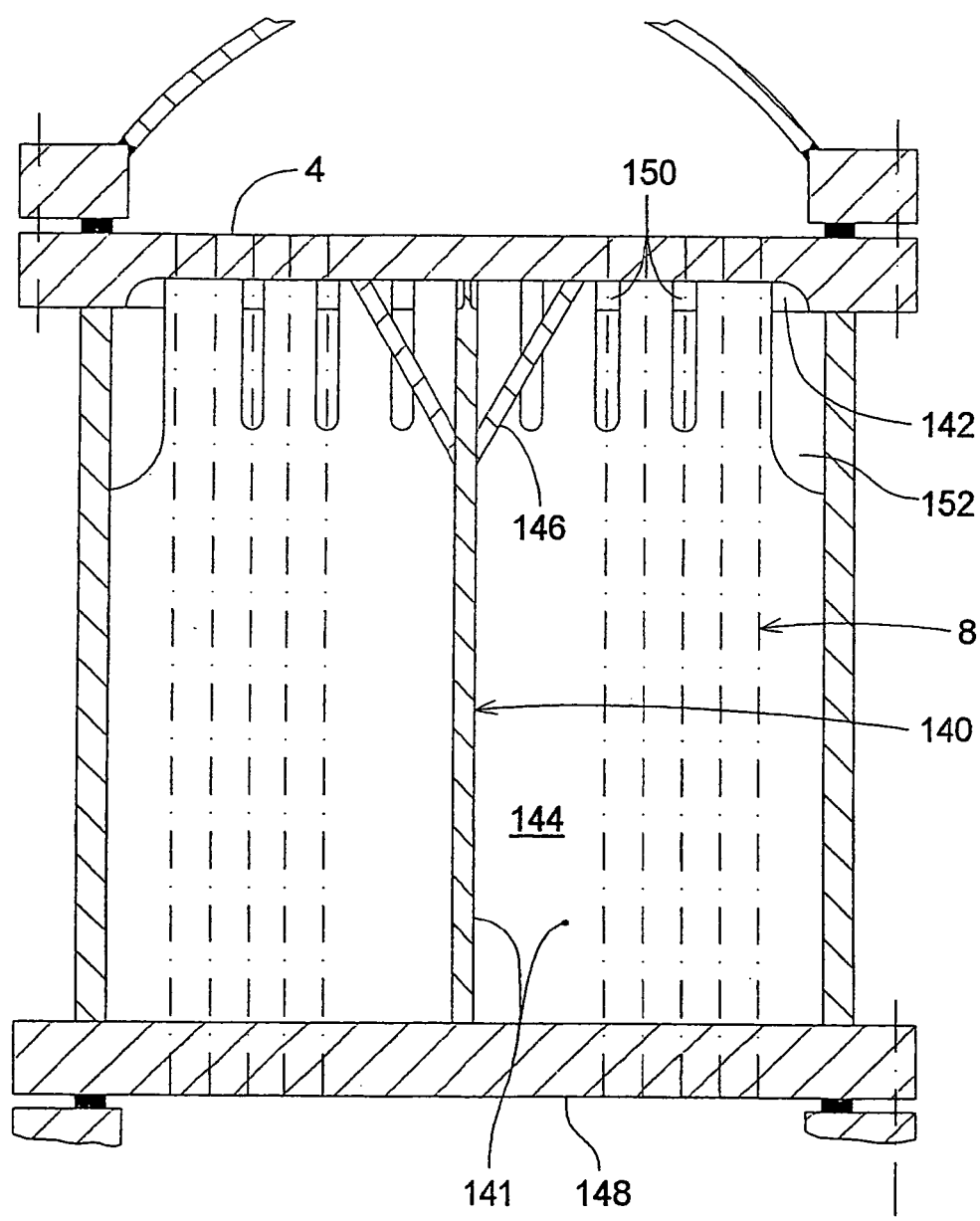
FIG. 8 shows a schematic drawing of a support arranged inside a shell-and-tube type reactor according to the invention, the support supporting in particular the gas intake-side tube sheet.

FIG. 8 shows how the tube sheet 4 on the gas intake side can be supported towards the gas output end of the reactor in the event that in the gas intake region a deflagration or even a detonation should occur. In the example shown there a corresponding support 140 is formed as a multi-winged metal component or is made of at least two radially extending metal components essentially formed by two sheets 141 standing in the shape of an x which, preferably loosely, engage into corresponding grooves 142 on the underneath of the tube sheet 4 and fit into corresponding radial lanes of the tube bundle 8. In addition the center of the tube sheet 4 can, as shown, be supported inside the tubeless medium region 144 near the tubing by means of diagonal struts or by a sheet metal cone 146 on the sheets 141. This makes it possible under certain circumstances to do with a single sheet 141 thus saving perhaps up to two tubeless lanes. In place of the sheet metal cone 146 one could also have a cylindrical, prismatic or pyramid-shaped metal component.

The support 140 may but need not, as shown, run through to the tube sheet 148 on the gas output side or to a separator plate. In any case, however, it must be in a position to guide the supporting forces into the reactor shell. To compensate the different heat expansions the sheets like the sheet 141 can have, especially in the vicinity of the gas intake-side tube sheet 4, longitudinally extending stress relief slots 150 as well as corresponding recesses 152 at their attachment to the reactor shell 6. Otherwise they may, wherever this could be functional for flow-technical reasons or to save weight, be pierced or replaced with a skeletal design. Resting the support 140 on the gas output side tube sheet 148 has, not least of all, the advantage that then even the latter is supported against deflagration pressure forces propagating through the tubing towards the gas output space or which could be generated there from a subsequent ignition.

According to DE 198 06 810 A1 the gas intake side tube sheet 4 can be heat-insulated (not shown) in order to keep the gas distribution space 14 "cool" and also to reduce tendencies towards deflagration or even detonation.

Figure 9:
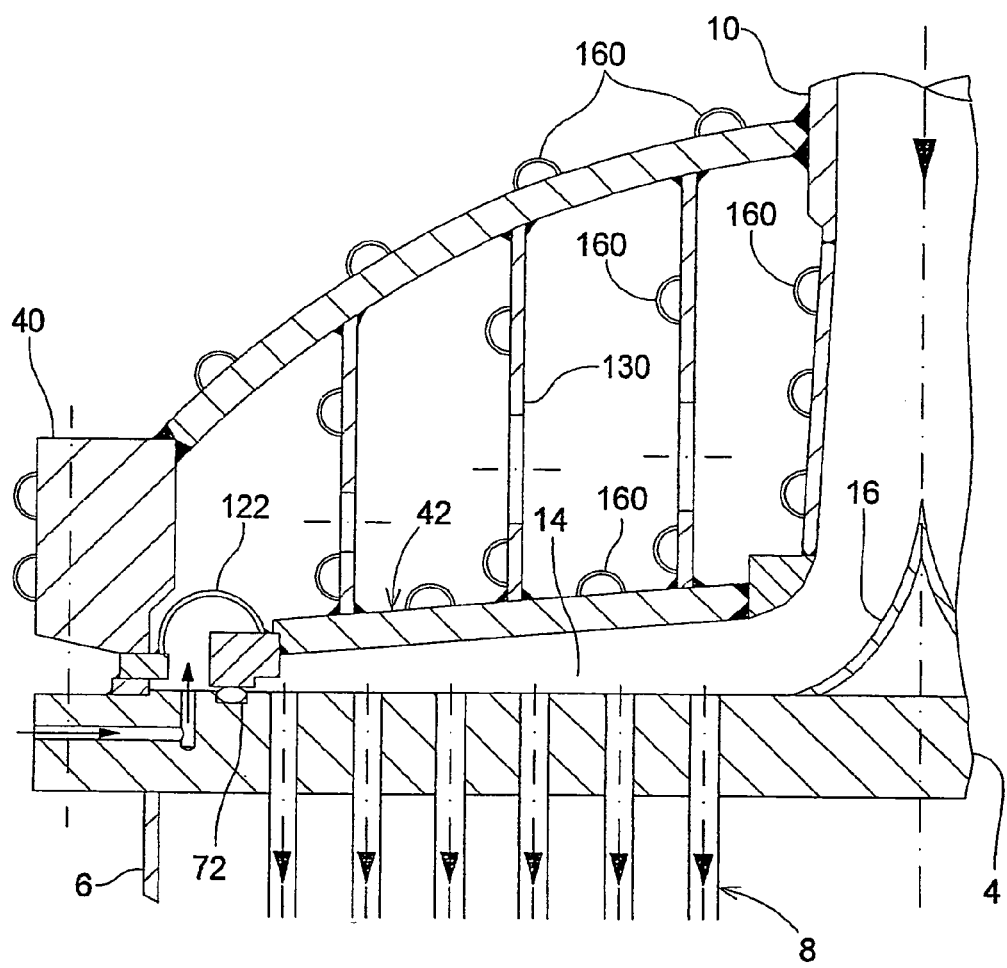
FIG. 9 shows a schematic drawing of a gas intake hood similar to the one in FIG. 5 with cooling and/or heating devices provided on it.

FIG. 9 provides for the same purpose—with an arrangement similar to that in FIG. 5 or FIG. 7—at various points in and on the gas intake hood 2 for coolant canals 160 which can, however and especially when the reactor is started up, also function as heat medium canals and can additionally contribute to reducing heat stresses.

Figure 10:
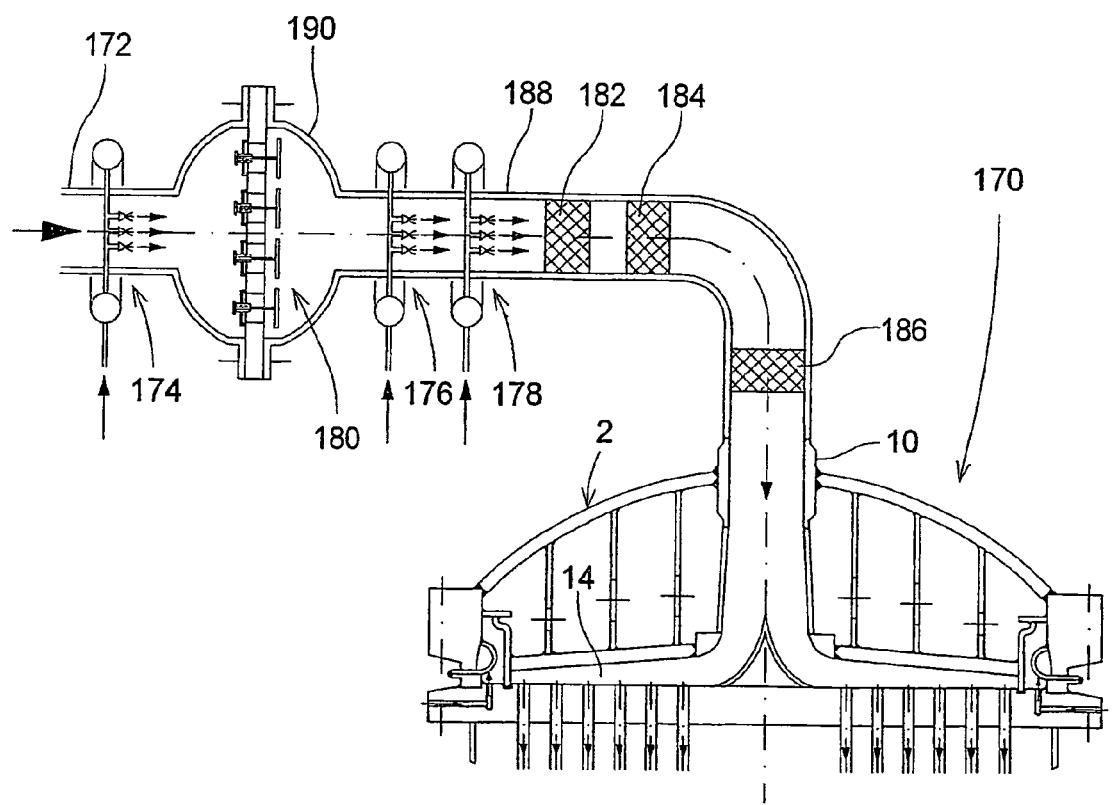
FIG. 10 shows a similar illustration as FIG. 7 with the devices preceding the process gas stream fed into the reactor.

FIG. 10 shows the gas intake end 170 of a shell-and-tube type reactor according to FIG. 7 with upstream facilities for preparation of process gas. In the example shown, at any given point 174 a second process gas component, such as a hydrocarbon gas, is fed into a main pipe 172 in which a suitable tempered process gas basic component flows under appropriate pressure, for example air, the so-called main flow. The second process gas component is fed in a quantity not rendering the process gas capable of deflagration while additional partial quantities of the second or even additional process gas components are added at 176 or 178 downstream of a check valve arrangement 180. At the latest after the feed-in point 178 the process gas is in the explosive range.

All of the process gas components fed in are subsequently mixed in several coordinates by means of several successive mixers 182, 184 and 186 and mixed gently, that is for instance with the greatest possible avoidance of turbulence. In addition care is taken in pipe routing to avoid any unevenness. Furthermore, the pipe 188 between the check valve arrangement 180 and the gas intake hood 2 is kept as short as possible to prevent the accumulation of high deflagration pressures. The check valve arrangement 180 prevents any blast wave generated in the pipe 188 or downstream therefrom from propagating further into the main pipe 172 and causing damages to the organs feeding into the latter. The check valve arrangement 180 is located in a chamber 190 simultaneously forming a desirable pressure relief volume for such a blast wave. The chamber 190 can have any shape and can contain a practically unlimited volume just as additional chambers can likewise be added at the same point. If required, the first feed-in point 174 can incidentally likewise be followed by a mixer (not shown), preferably in front of (i.e. upstream) the check valve arrangement 180. Nevertheless, the feed-in point 174 can be located far ahead of the check valve arrangement in order to attain in this way a favorable mixing. On the other hand, possibly downstream the check valve arrangement 180, a single additional feed-in point such as 176 and a single mixer could also be sufficient.

The check valve arrangement 180, the chamber 190, the pipe 188 and the mixers 182 through 186 included in them and the feed-in facilities as well as the reactor itself are all designed as to strength and stability to withstand the greatest deflagration or detonation pressures occurring in them. This applies, as stated, despite the previously described measures to avoid as much as possible detonations and also deflagrations.

Figure 11:
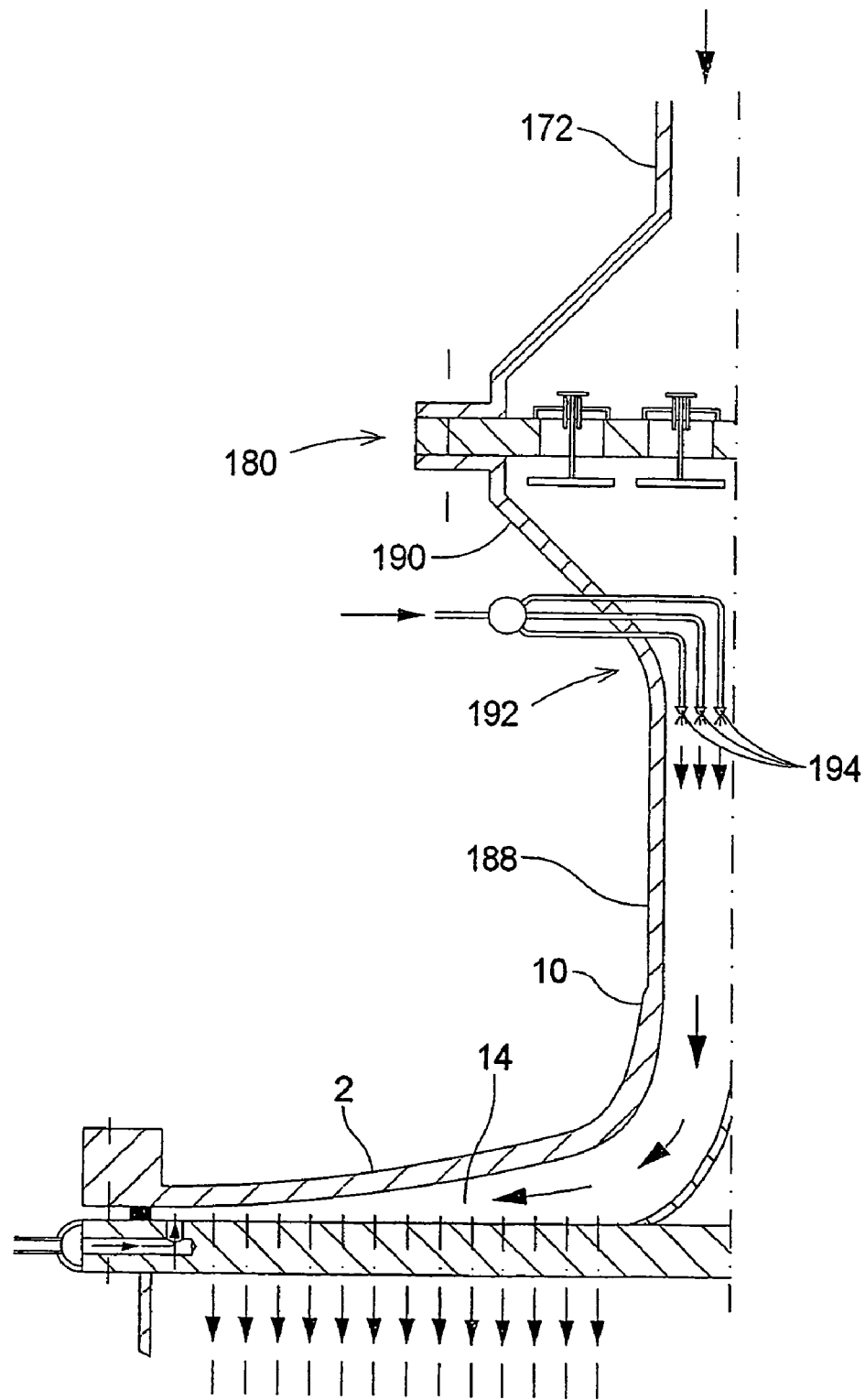
FIG. 11 shows a schematic drawing of an alternatve process gas feeding in connection with a gas intake hood according to FIG. 1.

FIG. 11 shows an arrangement in principle similar to that of FIG. 10 but in connection with a gas intake hood 2 according to FIG. 1, the mixers as well as a curvature in the pipe 188 being omitted, the pipe in this case being particularly short. Mixers entail in any case disturbances in gas flows, something that makes the relevant process gas even more susceptible to deflagration. For producing particularly deflagration-critical process gas mixtures one should therefore try to avoid mixers as much as possible. Moreover the possible starting or build-up length for the generation of a detonation should be shortened.

According to FIG. 11 the check valve arrangement 180 is disposed centered over the gas intake hood 2 on the axis of the gas intake pipe socket or nozzle 10, and instead of the two feed-in points 176 and 178 in FIG. 10 a single fine sparging point or device 192 is provided while there are no mixers. The fine sparging device 192 has a number of sparging units 194 distributed across the pipe cross-section, i.e. at least five but preferably 50 such sparging units 194 per m$^2$ or even more, and which can be designed to have nozzles and individual throttling devices similar to the sparging units on the contact tube entry according to DE 100 21 986 A1 and/or which are able to give the process gas components sparged in a twist. In this way, feed-in of the second process gas component, such as a hydrocarbon, is so finely distributed and regularly administered that there is no need for mixers for producing a homogeneous process gas flow.

In principle, the process gas components sparged in can be present in liquid or gaseous form, cold or heated-up. With liquids it is feasible to inject them by means of an inert gas. Either way, sparging can be done at high pressure in order to produce partial vaporization combined with break-up of the flow similar to the way this is practiced in feeding automotive fuel to the cylinder chamber of combustion engines.

The sparging zone can be furnished with a shell heater and accordingly the feed pipes for the second process gas can be heated or heat-insulated.

The design of the reactor components as to stability and strength depends on the type and concentration of the materials to be processed. It is usually undertaken for stationary operations. When starting up a shell-and-tube type reactor of the type described above care must consequently be taken that at no time the deflagration or detonation strength estimated for operations is exceeded. Normally one starts up with only one of the various process gas components (the main flow). When a certain mass flow of this has been attained then the second process gas component is added. If in the plant's operations itself an inert gas like CO2 is produced then startup can be accomplished by including it, essentially in accordance with EP 1 180 508 A1. Whether in starting up an inert gas is to be fed in additionally or whether the danger of deflagration and detonation severity can be reduced simply by varying pressure and temperature to operational levels is governed by the details of the process.

As already mentioned in the beginning, startup can and may entail the ignitable range. Just as in normal operation, also in startup besides the process gas composition other parameters such as, most especially, pressure and temperature, have to be taken into account. Both of them affect the deflagration and detonation behaviour. It is possible to vary pressure and temperature during startup. In that way, when starting up pressure can be reduced while the temperature in the gas distribution space 14 is raised. At the latest towards the end of the startup phase both are then adjusted to the operational levels intended.

If a shell-and-tube type reactor is run in the lower deflagration range, that is with only a minimal risk of deflagration and minor deflagration pressure to be taken into account, and if in doing so a recycle gas out of the reactor as inert gas is fed into the main flow, then startup can be accomplished in the following manner:

First via the main pipe 172 air or oxygen is fed in as the main flow. Then one starts feeding in a hydrocarbon flow via the sparging device 194 (FIG. 11). As long as the hydrocarbon concentration is low there is no risk of deflagration. The recycle gas recovered likewise basically consists only of materials from the main flow. As the startup process advances and hydrocarbons are added the reaction product is already being produced as the result of which the recycle gas already contains a portion of inert gas like carbon dioxide. In the further course of the startup process the hydrocarbon flow is increased. But since the main flow by then already contains a significant portion of the inert gas at no time a critical level is reached.

In principle, in this way the attempt is made to avoid the explosive range in the startup phase in order to enter into the explosive range only when sufficient process stability has been achieved.

In principle, the same applies as well to operations in the upper explosive range. Here, however, the hydrocarbon flow is normally administered via the feed pipe 172 as main flow while, for instance, oxygen is fed in via the sparging device 194.

According to the current level of know how, a shell-and-tube type reactor according to the invention can be advantageously used for oxidation, hydration, dehydration, nitration, alkylation and similar processes and then especially for the production of ketones, methyl-isobutyl-ketones, mercaptan, isoprene, anthrachinone, o-cresol, ethylene hexane, furfurol, acetylene, vinyl acetate, isopropyl chloride, naphthalene acid anhydride, vinyl chloride, oxo-alcohol, pyrotol, styrol, methanformic acid nitrile, polyphenylene oxide, dimethylphenol, pyridinaldehyde, Therban, alpha olefins, vitamin B6, prussic acid, aniline, formic acid nitrate, difluoromethane, 4-methyl-2-pentanon and tetrahydrofuran as well as in particular the oxidation of dimethylbenzols (m,o,p) into the corresponding monoaldehydes and dialdehydes, oxidation of dimethylbenzols (m,o,p) into the corresponding monocarbonic and dicarbonic acids or their anhydrides, oxidation of trimethylbenzols into the corresponding monoaldehydes, dialdehydes and trialdehydes, oxidation of trimethylbenzols into the corresponding monocarbonic acids, dicarbonic acids and tricarbonic acids or their anhydrides, oxidation of durol into pyromellitic acid anhydride, oxidation of gamma picoline or beta picoline into gamma picoline-carbo-aldehyd, oxidation of gamma picoline or beta picoline into iso-nicotinic acid or nicotinic acid, oxidation of propene into acrolein, oxidation of acrolein into acrylic acid, oxidation of propane into acrolein, oxidation of propane into acrylic acid, oxidation of butane into maleic acid anhydride, oxidation of refined product into maleic acid anhydride, oxidation of i-butenes into methacrolein, oxidation of methacrolein into methacrylic acid, oxidation of methacrolein into methyl-methacrylate, oxidation of i-butane into methacrolein, oxidation of i-butane into methacrylic acid, ammoxidation of dimethylbenzols (m,o,p) into the corresponding mononitriles and dinitriles, ammoxidation of trimethylbenzols into the corresponding mononitriles, dinitriles and trinitriles, ammoxidation of propane to acrylonitrile, ammoxidation of propene into acrylonitrile, ammoxidation of beta picoline into 3-cyanopyridine, ammoxidation of gamma picoline into 4-cyanopyridine, oxidation of methanol into formaldehyde, oxidation of naphthalene and/or o-xylol possibly mixed into phthalic acid anhydride, oxidation of ethane into acetic acid, oxidation of ethanol into acetic acid, oxidation of geraniol into citral, oxidation of ethene into ethyloxide, oxidation of propene into propylene oxide, oxidation of hydrogen chloride into chlorine, oxidation of glycol into glyoxal and hydration of maleic acid anhydride into butane diol.

A shell-and-tube type reactor according to the present invention presents among others the following features and advantages:

The volume of space available to the process gas prior to its entry into the contact tubes can be kept to a minimum according to design and technical flow vantage points.

The space volume available to the process gas prior to its entry into the contact tubes, dead spaces, in which the process gas could fully or partially come to rest, may be avoided as far as possible from design and technical-flow vantage points.

In administering at least the process gas already ready to react diversions and most especially unevenness may be avoided as much as possible.

The gas intake hood (2; 60) may be fastened to the edge of the tube sheet (4) on the gas intake side by means of studs.

The gas intake hood (2; 60) and/or its fitting (42) can be cooled and/or heated.

The gas intake hood (2; 60) and/or its fitting (42) may have canals (160) through which coolant or heat transfer medium can flow.

The support may have a number of longitudinally aligned pressure relief slots (150) and/or recesses (152).

The support may extend up to the tube sheet (148) on the gas output side.

The support is loosely joined to the tube sheet (4; 148) in question.

The support may fit into a recess (142) in the tube sheet (4; 148) in question.

There has thus been shown and described a novel shell-and-tube type reactor for carrying out catalytic gaseous phase reactions and a procedure for operating the same which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. Shell-and-tube type reactor for carrying out catalytic gaseous phase reactions, comprising (a) a bundle of contact tubes, through which the relevant reaction gas mixture flows, that extend between a gas intake-side tube sheet and a gas output-side tube sheet, that contain a catalytic filling, and that are flushed by a heat transfer medium inside a surrounding reactor shell; (b) a gas intake hood and a gas outlet hood spanning the two tube sheets, respectively, for providing the relevant process gas to the contact tubes; and (c) a process gas main pipe for feeding the process gas into the gas intake hood, the improvement wherein the process gas main pipe comprises a first section, in which the process gas is in a non-explosive range, and in process gas flow direction behind it a second section, in which the process gas is in an explosive range; wherein the process gas main pipe comprises in its first section a check valve arrangement; and wherein the check valve arrangement and the gas intake-side tube sheet, and all parts therebetween, which bear the process gas pressure under normal operation conditions, are designed to withstand the maximum pressure caused by a deflagration or detonation.

2. Shell-and-tube type reactor according to claim 1, wherein the check valve arrangement comprises at least two paralleled check valves.

3. Shell-and-tube type reactor according to claim 1, wherein the process gas main pipe comprises at least one feed-in point for feeding in at least one of a partial quantity of, and a component of, the process gas, due to which the process gas passes from the non-explosive range into the explosive range.

4. Shell-and-tube type reactor according to claim 1, further comprising a device for injecting a flushing gas into dead spaces, in which the process gas prior to its entry into the contact tubes could otherwise fully or partially come to rest, the flushing gas being inert in relation to the relevant reaction.

5. Shell-and-tube type reactor according to claim 4, wherein flushing gas is injected radially outside of the contact tube bundle at the edge of the tube sheet on the gas intake side.

6. Shell-and-tube type reactor according to claim 5, wherein the flushing gas is injected with a tangential flow component.

7. Shell-and-tube type reactor according to claim 1, wherein the gas intake hood is designed flat and funnel-shaped and with a distance to the gas intake-side tube sheet, which decreases in the radially outward direction, and with a central gas intake.

8. Shell-and-tube type reactor according to claim 7, wherein the gas intake hood is rounded off at least approximately like a trumpet funnel and flattens out towards the edge.

9. Shell-and-tube type reactor according to claim 1, further comprising a flat funnel-shaped fitting arranged coaxially in a shell-shaped gas intake hood from which a central pass-through is connected, said fitting being sealed with respect to the gas intake hood, and the edge of said fitting being sealed towards the edge of the tube sheet on the gas intake side.

10. Shell-and-tube type reactor according to claim 9, wherein the fitting is rounded off at least approximately like a trumpet funnel and flattens out towards the end.

11. Shell-and-tube type reactor according to claim 9, wherein the fitting is supported at a plurality of points on the gas intake hood.

12. Shell-and-tube reactor according to claim 11, wherein the points are substantially regularly spaced.

13. Shell-and-tube type reactor according to claim 9, wherein the seal on the edge of the fitting is to a limited extent gas-permeable and further comprising a device for injecting a flushing gas over the seal.

14. Shell-and-tube type reactor according to claim 13, wherein the seal on the edge of the fitting comprises a partially permeable material.

15. Shell-and-tube type reactor according to claim 13, wherein the seal on the edge of the fitting has discrete gas penetration channels.

16. Shell-and-tube type reactor according to claim 13, wherein the seal on the edge of the fitting comprises a profile which is flexible under high pressure.

17. Shell-and-tube type reactor according to claim 13, wherein the seal on the edge of the fitting is connected on the outside with a space through which the flushing gas is fed.

18. Shell-and-tube type reactor according to claim 17, wherein the space is limited by a radially inside seal and a radially outside seal.

19. Shell-and-tube type reactor according to claim 18, wherein the flushing gas is under substantially high pressure than the external atmosphere.

20. Shell-and-tube type reactor according to claim 17, wherein the space includes the residual space of the gas intake hood.

21. Shell-and-tube type reactor according to claim 9, wherein at least one of the gas intake hood, the tube sheet on the gas intake side and the fitting are connected to each other via a welded lip seal.

22. Shell-and-tube type reactor according to claim 1, wherein a spike-shaped flow diverter is arranged on the tube sheet on the gas intake side, pointed towards the gas intake and narrowing down in that direction.

23. Shell-and-tube type reactor according to claim 1, wherein a support for the gas intake-side tube sheet is disposed between the gas intake-side tube sheet and the gas output-side tube sheet and is mounted to the reactor shell.

24. Shell-and-tube type reactor according to claim 23, wherein the support at least in part comprises two metal components which extend radially outwardly from the reactor's longitudinal axis.

25. Shell-and-tube type reactor according to claim 24, with a ring-shaped contact tube bundle, wherein the support partially comprises an additional metal component in the tubeless interior of the contact tube bundle, said additional metal component in turn being supported by the radial metal components, said additional metal component having a shape selected from the group consisting of substantially cylindrical, prismatic, conic and pyramid-shaped.

26. Shell-and-tube type reactor according to claim 1, wherein the tube sheet on the gas intake side is heat-insulated.

27. Shell-and-tube type reactor according to claim 1, wherein a first process gas component flows in the process gas main pipe and the process gas main pipe comprises in the process gas flow direction prior to the gas intake hood a first feed-in point for a second process gas component to be added to the first process gas component and thereafter at least one second feed-in point for the rest of the second or an additional process gas component.

28. Shell-and-tube type reactor according to claim 27, wherein at least one mixer follows the last feed-in point.

29. Shell-and-tube type reactor according to claim 27, wherein at least one second feed-in point is formed by a fine sparging device with a number of sparging units distributed across the cross-section of the channel.

30. Shell-and-tube type reactor according to claim 29, wherein at least one of the sparging units include individual throttling devices and devices producing a twist.

31. Shell-and-tube type reactor according to claim 27, wherein at least one of the feed-in points is arranged to receive the associated process gas component in a liquid form.

32. Shell-and-tube type reactor according to claim 31, wherein said at least one feed-in point has means for injecting the liquid process gas component.

33. Shell-and-tube type reactor according to claim 31, wherein said at least one feed-in point is positioned such that the liquid process gas component is at least one of atomized and vaporized.

34. Shell-and-tube type reactor according to claim 31, wherein said at least one feed-in point has at least one of heating devices and heat insulation.

35. Shell-and-tube type reactor according to claim 27, wherein the check valve arrangement is located between the first and the second feed-in point.

36. Shell-and-tube type reactor according to claim 27, wherein a pressure reduction space is located between the first and the second feed-in point.

37. Shell-and-tube type reactor according to claim 36, wherein the pressure reduction space is formed at least partially by a chamber housing the check valve arrangement.

38. A method of using the shell-and-tube type reactor according to claim 1, comprising the step of carrying out gas-phase reactions for one of the group of processes consisting of oxidation, hydration, dehydration, nitration and alkylation.

39. The method of using the shell-and-tube type reactor according to claim 38, for providing a composition of matter selected from the group consisting of ketones, methyl-isobutyl-ketones, mercaptan, isoprene, anthrachinone, o-cresol, ethylene hexane, furfurol, acetylene, vinyl acetate, isopropyl chloride, naphthalene acid anhydride, vinyl chloride, oxo-alcohol, pyrotol, styrol, methanformic acid nitrile, polyphenylene oxide, dimethylphenol, pyridinaldehyde, Therban, alpha olefins, vitamin B6, prussic acid, aniline, formic acid nitrate, difluoromethane, 4-methyl-2-pentanon and tetrahydrofuran.

40. The method of using the shell-and-tube type reactor according to claim 1, comprising the step of carrying out gas-phase reactions for one of the group of processes consisting of oxidation of dimethylbenzols (m,o,p) into the corresponding monoaldehydes and dialdehydes, oxidation of dimethylbenzols (m,o,p) into the corresponding monocarbonic and dicarbonic acids or their anhydrides, oxidation of trimethylbenzols into the corresponding monoaldehydes, dialdehydes and trialdehydes, oxidation of trimethylbenzols into the corresponding monocarbonic acids, dicarbonic acids and tricarbonic acids or their anhydrides, oxidation of durol into pyromellitic acid anhydride, oxidation of gamma picoline or beta picoline into gamma picoline-carbo-aldehyd, oxidation of gamma picoline or beta picoline into iso-nicotinic acid or nicotinic acid, oxidation of propene into acrolein, oxidation of acrolein into acrylic acid, oxidation of propane into acrolein, oxidation of propane into acrylic acid, oxidation of butane into maleic acid anhydride, oxidation of refined product into maleic acid anhydride, oxidation of i-butenes into methacrolein, oxidation of methacrolein into methacrylic acid, oxidation of methacrolein into methyl-methacrylate, oxidation of i-butane into methacrolein, oxidation of i-butane into methacrylic acid, ammoxidation of dimethylbenzols (m,o,p) into the corresponding mononitriles and dinitriles, ammoxidation of trimethylbenzols into the corresponding mononitriles, dinitriles and trinitriles, ammoxidation of propane to acrylonitrile, ammoxidation of propene into acrylonitrile, ammoxidation of beta picoline into 3-cyanopyridine, ammoxidation of gamma picoline into 4-cyanopyridine, oxidation of methanol into formaldehyde, oxidation of naphthalene and/or o-xylol possibly mixed into phthalic acid anhydride, oxidation of ethane into acetic acid, oxidation of ethanol into acetic acid, oxidation of geraniol into citral, oxidation of ethene into ethyloxide, oxidation of propene into propylene oxide, oxidation of hydrogen chloride into chlorine, oxidation of glycol into glyoxal and hydration of maleic acid anhydride into butane diol.

41. A process for operating a shell-and-tube type reactor according to claim 1, wherein the shell-and-tube type reactor is run in production operations with such a charge of a first process gas component with at least one further process gas component with which occasional deflagrations or even detonations may occur.

42. A process for operating a shell-and-tube type reactor according to claim 1, wherein for starting up the reactor the concentrations of the process gas components and possibly additional parameters as well are measured on an ongoing basis in such a way that the violence of deflagrations or even detonations occurring does not exceed that what is anticipated for operating conditions.

43. Shell-and-tube type reactor according to claim 14, wherein said material is graphite tissue.

44. Shell-and-tube type reactor according to claim 15, wherein said channels are drill holes.

45. Shell-and-tube type reactor according to claim 15, wherein said channels are furrows.

* * * * *